(12) United States Patent
Nimitz

(10) Patent No.: US 9,616,124 B2
(45) Date of Patent: Apr. 11, 2017

(54) ANTIVIRAL SUPPLEMENT COMPOSITIONS AND METHODS OF USE

(71) Applicant: Jonathan S. Nimitz, Albuquerque, NM (US)

(72) Inventor: Jonathan S. Nimitz, Albuquerque, NM (US)

(*) Notice: Subject to any disclaimer, the term of this patent is extended or adjusted under 35 U.S.C. 154(b) by 0 days.

(21) Appl. No.: 14/333,645

(22) Filed: Jul. 17, 2014

(65) Prior Publication Data

US 2016/0015762 A1    Jan. 21, 2016

(51) Int. Cl.
*A61K 33/30*     (2006.01)
*A61K 45/06*     (2006.01)
*A61K 36/185*    (2006.01)
*A61K 31/716*    (2006.01)
*A61K 36/254*    (2006.01)

(52) U.S. Cl.
CPC .......... *A61K 45/06* (2013.01); *A61K 31/716* (2013.01); *A61K 33/30* (2013.01); *A61K 36/185* (2013.01); *A61K 36/254* (2013.01)

(58) Field of Classification Search
None
See application file for complete search history.

(56) References Cited

U.S. PATENT DOCUMENTS

| | | |
|---|---|---|
| 6,596,313 B2 | 7/2003 | Rosenbloom |
| 6,793,942 B2 | 9/2004 | Gelber |
| 6,827,945 B2 | 12/2004 | Rosenbloom |
| 7,579,024 B2 | 8/2009 | Morrissey |
| 7,682,616 B2 | 3/2010 | Rangel |
| 7,867,523 B2 | 1/2011 | Vanterpool |
| 8,637,094 B2 | 1/2014 | Kiani |
| 8,697,670 B2 | 4/2014 | Remmereit |
| 8,703,174 B2 | 4/2014 | Hurwitz |
| 2002/0111382 A1* | 8/2002 | Cui ................. A61K 31/235 514/533 |
| 2004/0076641 A1* | 4/2004 | Kershenstine, Jr. .. A23L 1/3002 424/195.15 |
| 2008/0219964 A1* | 9/2008 | Keefe ................ A23L 1/30 424/94.2 |
| 2009/0060879 A1* | 3/2009 | Clymer ............ A61K 31/592 424/93.4 |
| 2010/0112096 A1 | 5/2010 | Herrmann |
| 2010/0113373 A1 | 5/2010 | Phillips |

OTHER PUBLICATIONS

Heikkinen, T. et al., The common cold. Lancet. 2003;361:51-9.
Fendrick, A.M., Viral respiratory infections due to rhinoviruses: current knowledge, new developments. American Journal of Therapeutics 2003;10:193-202.
Lee, R. et al., Flu for You? The Common Cold, Influenza, and Traditional Medicine, Explore, May 2006, vol. 2, No. 3. pp. 252-255.
Buhner, S., Herbal Antivirals. North Adams, MA: Storey Publishing, 2013, pp. 22-60.
Williams, J.E., Viral Immunity. Charlottesville, VA: Hampton Roads Publishing, 2002, pp. 300-318.
Williams, J.E., Beating the Flu. Charlottesville, VA: Hampton Roads Publishing, 2002, pp. 95-113.
McCutcheon, A.R. et al. Antiviral screening of British Columbian medicinal plants. Journal of Ethnopharmacology Dec. 1, 1995;49(2):101-10.
Mukhtar, M. et al., Antiviral potentials of medicinal plants, Virus Research 131 (2008) 111-120.
Instant Immunity. Printed Oct. 7, 2014. "Instant Immunity: How it Works" http://www.instantimmunity.com/#how.
Shopfagen.com. Printed Oct. 7, 2014. "Loviral product description and details" http://www.shopfagen.com/catalog/loviral-60-softgels.html.
Vitamins Because Your Worth It. Printed Oct. 7, 2014. "Immune Defense Advantage" http://www.doctorvitaminstore.com/8077_ImmuneDefensePg2.html.
Herb Pharm. Printed Oct. 7, 2014. "Virattack" https://www.herb-pharm.com/store/product_info.php?products_id=241.
Rockwell Nutrition. Printed Oct. 7, 2014. "Astragalus Combination #1 by Genestra" http://www.rockwellnutrition.com/astragalus-combination-1-by-genestra.html#.VDRmYr67b4c.
Planetary Herbals. Printed Oct. 7, 2014. "Yin Chiao-Echinacea Complex" http://www.planetaryherbals.com/products/print/GP1564/.
Acupuncture Atlanta. Printed Oct. 7, 2014. "Astra Isatis" http://www.acuatlanta.net/health-concerns-astra-isatis-270-count-p-17676.html.
Golden Needle. Printed Oct. 7, 2014. "Isatis 6" http://www.goldenneedleonline.com/Isatis-6-100-tablets.html.
iHerb.com. Printed Oct. 7, 2014."Swedish Herbal Institute Kan Jang Plus" http://www.iherb.com/Swedish-Herbal-Institute-Kan-Jang-Plus-Immune-Support-Formula-30-Capsules/36207.
Generationrescue.org. Printed Oct. 7, 2014. "ViraStop 2X" https://www.generationrescue.org/assets/Grant-Resources/RFG-3-ViraStop2x.pdf.
Tailor Made Nutrition. Printed Oct. 7, 2014. "NuMedica Immunographis Supplement Facts" http://www.tallormadenutrition.com/shop/immunographis-p-11333.
Amazon.com UK. Printed Oct. 7, 2014. "Hawaiipharm Immune Care Liquid Extract Tincture" http://www.amazon.co.uk/HawaiiPharm-Immune-Care-Liquid-Extract/dp/B00A8FEC1A.
Hospitalopedia. Printed Oct. 7, 2014. "Viro Plus" http://hospitalopedia.com/viro-plus.
Four Winds Nutrition. Printed Oct. 7, 2014. "Virustat" http://www.webnat.com/proddetail.asp?prod=virustat.
HerbsPro. Printed Oct. 7, 2014. "Lomatium Osha Throat Spray" http://www.herbspro.com/lomatium-osha-throat-spray-32029.html.
ITM Online. Printed Oct. 7, 2014. "Shuanghuanglian: Potent Anti-Infection Combination of Lonicera, Forsythia, and Scute" http://www.itmonline.org/arts/shuang.htm.

(Continued)

Primary Examiner — Terry A McKelvey
Assistant Examiner — Catheryne Chen

(57) ABSTRACT

The present invention relates to the field of dietary supplements, and in particular to antiviral compositions and methods of use. Compositions are described involving various combinations of *Andrographis, Astragalus, Eleuthero, Isatis, Lomatium, Pelargonium, Sambucus, Scute*, and/or Zinc, optionally with additional components. These combinations of supplements synergistically reduce both severity and duration of viral infections, including in particular colds and influenza, as well as providing additional benefits.

24 Claims, No Drawings

(56) References Cited

OTHER PUBLICATIONS

Vitacost. Printed Oct. 7, 2014. "Metagenics Essential Defense Supplement Facts" http://www.vitacost.com/metagenics-essential-defense.
Vitacost. Printed Oct. 7, 2014. "Gaia Herbs RapidRelief Quick Defense Supplement Facts" http://www.vitacost.com/gaia-herbs-rapidrelief-quick-defense-20-liquid-capsules-1.
Swanson Health Products. Printed Oct. 7, 2014. "Airborne immune support supplement" http://www.swansonvitamins.com/airborne-triple-pack-effervescent-zesty-orange-30-tabs.
1stChineseHerbs.com. Printed Oct. 7, 2014. "Serious Effective Cold and Flu Tablets Zhong Gan Ling" http://www.1stchineseherbs.com/zhong_gan_ling.html.
Source Naturals. Printed Oct. 7, 2014. "Wellness Cold & Flu Supplement Facts" http://www.sourcenaturals.com/products/GP1339.
Source Naturals. Printed Oct. 7, 2014. "Wellness FluGuard Supplement Facts" http://www.sourcenaturals.com/products/GP2064.
Source Naturals. Printed Oct. 7, 2014. "Wellness Shot Supplement Facts" http://www.sourcenaturals.com/products/GP2386/.
Source Naturals. Printed Oct. 7, 2014. "Wellness Immune Chewable Supplement Facts" http://www.sourcenaturals.com/products/GP2304.
Source Naturals. Printed Oct. 7, 2014. "Wellness Formula Tablet Supplement Facts" http://www.sourcenaturals.com/products/GP1345.
Source Naturals. Printed Oct. 7, 2014. "Wellness Formula Capsule Supplement Facts" http://www.sourcenaturals.com/products/GP1345.
NOW Foods. Printed Oct. 7, 2014. "Elderberry & Zinc Lozenges" http://www.nowfoods.com/Elderberry-and-Zinc-90-Loz.htm.
Vitacost. Printed Oct. 7, 2014. "Zand Elderberry Zinc Lozenges Supplement Facts" http://www.vitacost.com/zand-herbalozenge-zinc-sweet-elderberry.
Umcka.com. Printed Oct. 7, 2014. "Umcka® Elderberry Intensive Cold+Flu" http://www.umcka.com/ColdFlu/15845-Umcka-Elderberry-Intensive-ColdFlu.aspx.
Zakay-Rones, Z., et al. Randomized study of the efficacy and safety of oral elderberry extract in the treatment of influenza . . . J. Intl. Medical Research (2004)32.2: 132-140.
Merluzzi, V.J. et al. Evaluation of zinc complexes on the replication of rhinovirus 2 in vitro. Research Communications in Chemical Pathology and Pharmacology 1989;66:425-40.
Novick, S.G., et al. How does zinc modify the common cold? Clinical observations and implications regarding mechanisms of action. Medical Hypotheses 1996;46:295-302.
Farr, B.M., et al. Two randomized controlled trials of zinc gluconate lozenge therapy of experimentally induced rhinovirus colds. Antimicrob. Agents Chemother. 1987;31:1183-7.
Eby, G.A., Zinc lozenges as cure for the common cold. Medical Hypotheses (2010) 74:482-92.
Hemila, H., Zinc lozenges may shorten the duration of colds: a systematic review. Open Respiratory Medical Journal (2011) 5:51-8.
Jin, M. et al., Structural features and biological activities of the polysaccharides from Astragalus membranaceus, Intl. J. of Biological Macromolecules Mar. 2014, 64:257-266.
Moore, M., Medicinal Plants of the Pacific West. Santa Fe: Red Crane Books, 1993, pp. 167-171.
Lizogub V.G. et al. Efficacy of a pelargonium sidoides preparation in patients with the common cold. Explore (NY). Nov.-Dec. 2007; 3(6):573-84.
Nagai, T. et al. Antiviral activity of plant flavonoid, 5,7,4'trihydroxy-8-methoxyflavone, from the roots of Scutellaria . . . Biological and Pharmaceut. Bull. 1995;18:295-299.
Baylor, N.W. et al., Inhibition of human T cell leukemia virus by the plant flavonoid baicalin (7-glucuronic acid, 5,6-dihydroxyflavone). J. of Infect. Diseases 1992;165:433-7.
Wang, Q. et al. Zinc coupling potentiates anti-HIV-1 activity of baicalin. Biochemical and Biophysical Research Communications 324 (2004) 605-610.
Lee, K.Y., et al. Macrophage activation by polysaccharide isolated from Astragalus membranaceus. International Immunopharmacology, vol. 5, Issues 7-8, Jul. 2005, pp. 1225-1233.
Vogler, B.K., et al. The efficacy of ginseng. A systemic review of randomized clinical trials. European Journal of Clinical Pharmacology 1999;55:567-75.
Steinmann, G.G. et al. Immunopharmacological in vitro effects of Eleutherococcus senticosus extracts. Arzneimittelforschung Jan. 2001: 51(1) 76-83.
Bohn, B. et al. Flow-cytometric studies with eleutherococcus senticosus extract as an immunomodulatory agent. Arzneimittelforschung 1987; 37(II), 10: 1193-6.
Nagai, T. et al., In vivo anti-influenza virus activity of plant flavonoids possessing inhibitory activity for influenza virus sialidase. Antiviral Research 1992;19:207-217.

\* cited by examiner

ANTIVIRAL SUPPLEMENT COMPOSITIONS AND METHODS OF USE

CROSS-REFERENCES TO RELATED APPLICATIONS

Not applicable

FIELD OF THE INVENTION

The present invention is directed to compositions and methods of use of combinations of dietary supplements that synergistically reduce both severity and duration of viral infections, in particular those of the upper respiratory tract.

BACKGROUND OF THE INVENTION

More than 400 different viruses are known to cause human diseases. These diseases include, for example, the common cold, influenza, cold sores (Herpes Type 1), genital herpes (Type 2), norovirus, mononucleosis, shingles, hepatitis, dengue, West Nile fever, severe acute respiratory syndrome (SARS), Hantavirus, Ebola, and acquired immunodeficiency syndrome (AIDS). Especially in the cases of the common cold and influenza, rapid mutations make it difficult for the body's immune system to identify and react to the invading viruses quickly.

To treat bacterial infections a variety of antibiotic drugs are available. However, for viral infections in general, and upper respiratory viral infections in particular, effective drugs to hinder reproduction of the infectious agents are much less available. Prescription anti-flu drugs currently available may reduce the duration of flu by about a day but in many cases do not reduce complications such as pneumonia, and often viruses are resistant to the drugs. The drugs must also be taken within the first 48 hours of flu symptoms.

During the H1N1 flu epidemic of 2009, a vaccine had not yet been produced, governments stockpiled antiviral drugs, and both were unavailable directly to the general public. In the event of a pandemic of an even more serious respiratory viral infection, the Centers for Disease Control and Prevention (CDC) and others have warned that health care facilities would be rapidly overwhelmed with patients, for whom they would have inadequate supplies and could do little.

On average, an adult American suffers from about two or three colds a year. The course of the disease normally lasts 7-10 days, usually starting with a mild sore throat, progressing to severe sore throat, fever, congestion, and fatigue. Flu has more severe symptoms, that may add to the previous list fever, chills, headaches, and body aches, and usually lasts 7-14 days. Sometimes serious complications such as pneumonia can develop. During the contagious period there is high risk of infecting other family members, friends, and members of the general public The CDC has estimated that in the United States, on average during the 1990s, about 36,000 people died of seasonal flu-related causes every year. On rare occasions flu viruses develop into especially virulent strains. For example, the flu pandemic of 1918 killed an estimated 50 million people worldwide, many of whom were otherwise strong and healthy.

Besides the death toll every year, colds and flu cause a great deal of discomfort and lost work. The CDC estimates that there are 30 million cases of seasonal flu annually in the U.S., and about 70 million workdays are lost due to colds and flu annually, with an economic cost in lost productivity of three to twelve billion dollars a year. According to the CDC, the number of schooldays lost by kindergarten through 12th-grade students annually in the U.S. due to colds is about 22 million, and to flu about 38 million. Even a 10% reduction in these losses would be highly significant and valuable. The present invention, if widely used, would allow a much greater reduction than this in both severity and duration of colds and flu.

Many people choose to have annual flu shots, but these must be tailored to specific strains selected a year in advance, must be repeated every year, and are only about 80% effective, because of the mutating strains of the influenza virus.

Although medical researchers are working hard on ways to combat viral infections, and are making progress, standard Western medicine at this time offers no cure for viral upper respiratory tract infections once contracted.

Many allopathic and herbal products are designed for temporary relief of symptoms without addressing the underlying infection. Conventional methods of treating a cold or flu have focused on such methods as rest, drinking liquids, gargling with salt water, and taking antihistamines, decongestants, and analgesics. There are also herbal and homeopathic products designed to relieve symptoms for a few hours. However, none of these methods can significantly decrease the viral load or overall duration of the infection.

In contrast, the purpose of the present invention is to eliminate the viruses from the body. The driving force for the present invention was the desire to develop a more effective method of treating colds and flu. Better remedies are needed to combat these infections, and it would be especially desirable if these remedies are low cost and non-prescription, that can be kept on hand or obtained quickly, to take at the first warning sign of a cold or flu.

BRIEF SUMMARY OF THE INVENTION

This invention describes new compositions of dietary supplements and methods of use for effectively and synergistically inhibiting viral reproduction and therefore significantly reducing symptoms of viral infections to a much greater extent than expected from a simple additive effect. In particular, certain embodiments of this invention greatly reduce both the severity and duration of viral upper respiratory tract infections.

Because these supplement compositions have general antiviral and immune-boosting properties, the present invention may find use in combatting many types of viral infections such as, without limitation, the common cold, influenza, norovirus, cold sores (Herpes Type 1), genital herpes (Type 2), norovirus, mononucleosis, shingles, hepatitis, dengue, West Nile fever, SARS, Ebola, Hantavirus, and AIDS. The present invention may also find use in treating viral infections of animals.

In various embodiments of the present invention, different combinations of components are provided. These are selected from the group consisting of *Andrographis, Astragalus, Eleuthero, Isatis, Lomatium, Pelargonium, Sambucus, Scute*, and Zinc.

DETAILED DESCRIPTION OF THE INVENTION

In general a supplement can contain both an herbal portion and a non-herbal portion. The herbal portion of a supplement consists of ingredients obtainable from plants. These may include, for example, without limitation, powdered root, stem, leaves, flowers, berries, extracts, isolates, and chemicals isolated from plants. Chemicals isolated from plants can include vitamins such as Vitamin C and antiviral chemicals such as andrographolide, astragalosides, baicalin, eleutherosides, and umckalin. The non-herbal portion of a supplement may contain, for example, minerals, vitamins derived from animal sources, and excipients.

Excipients are inactive components used in manufacturing capsules, tablets, softgels, lozenges, powders, syrups, extracts, and nasal sprays. These may include, for example, without limitation: alcohol, artificial colors, artificial flavors, citric acid, corn starch, dextrin, dibasic calcium phosphate, fructose, gelatin, hydroxypropylmethylcellulose, magnesium stearate, malic acid, maltodextrin, mannitol, microcrystalline cellulose, modified cellulose gum, natural colors, natural flavors, silica, sorbitol, stearic acid, sucrose, and xylitol.

An effective antiviral dose is the quantity of an antiviral substance sufficient to significantly inhibit viral reproduction. The daily dosage is the sum of the individual dosages given during the day, usually given in one to five separate doses. Doses may be provided in the form of tablets, capsules, lozenges, chewable compositions, troches, hard candies, oral sprays, nasal sprays, gels, powders, extracts, isolates, elixirs, syrups, teas, decoctions, liquid solutions, liquid suspensions, and sterilized solutions for injection. Common daily dosages of each component are listed after their descriptions below.

The present invention is a combination of components selected from the group consisting of *Andrographis, Astragalus, Eleuthero, Isatis, Lomatium, Pelargonium, Sambucus, Scute*, and Zinc. The present invention combines components in a novel and synergistic way that provides significantly better performance than use of the components individually, or than expected from their combination.

The unexpected result is that combining several of these components produces synergistic effects on inhibiting viral replication. A small series of human tests has revealed the surprising result that the present invention can in most cases reduce both symptoms and duration by greater than 80% compared with the normal course of cold or flu, significantly greater reduction than the 30-40% expected from the additive effects of the separate components of the invention.

Over the course of several years the present inventor and his immediate family members have voluntarily tested several embodiments of the invention on themselves on a dozen occasions. A test began when a family member noticed a worsening sore throat, a probable sign of an impending cold or flu.

In nine of twelve cases (75%) the symptoms were limited to a minor sore throat, which ended about one day after treatment began. For all nine of these cases both duration and severity were reduced by greater than 80%. It should be noted that in all previous cases, without the present invention, when any of the subjects had noticed an increasingly sore throat it developed rapidly into a cold or flu.

In the three remaining cases (25%), which included one case of probable H1N1 flu, there were additional symptoms lasting a total of three to four days before complete recovery. These three cases still showed over 50% improvement compared to the normal expected duration and severity of disease, again greater reduction than expected from additive effects.

These results all demonstrated synergism of the combined components. However, even more effectiveness was desired against the more difficult cases, and the invention has been significantly improved to provide additional antiviral activity, in particular against influenza.

The effects of the composition can be seen in the following ways. If administered to a person with early signs of a cold or flu, the viral load decreases while the symptoms remain mild, do not worsen significantly, and disappear rapidly. Controlled clinical in vitro, animal, and human testing is expected to verify and further quantify the effects, as well as determine the range of activity against different types of viral infections. Standard in vitro assays for influenza virus inhibitors include evaluation of inhibition of viral plaques, viral cytopathic effects, viral hemagglutinin, and viral yield. It is expected that these tests will confirm the therapeutic effects, including a significant drop in viral count, plus a synergistic reduction in severity and duration of infections.

The present invention is not designed as a preventive or palliative measure, but to assist the body's immune system in eliminating the viral infection. It is therefore qualitatively different from, and superior to, use of individual herbal or homeopathic products, other herbal blends, and other products designed to minimize symptoms without eliminating the infection.

Components from several traditions on four continents have been combined in new and synergistic ways in the present invention. The components have been selected from indigenous medicines with European, Chinese, East Indian, Native American, and African origins.

Up to nine components, in various combinations, make up the present invention. In simple cases two or three components will suffice, while in other more serious cases up to all nine components may be required for optimum effectiveness. The novel compositions are created by combining components selected from the group consisting of: *Andrographis, Astragalus, Eleuthero, Isatis, Lomatium, Pelargonium, Sambucus, Scute*, and Zinc.

Each component has a number of common and/or scientific names, which can be used interchangeably, some of which are listed below in the descriptions of the components. For simplicity throughout this application, the first (bold), short form of the name will be used to refer to each component.

Also, for brevity and simplicity, when the name of a plant is used in the context of the present invention, it means a dose of the active antiviral component(s) obtainable from that plant. For example, the phrase "a composition containing *Andrographis*" means a composition containing an antiviral dose obtainable from the *Andrographis* plant, which could be, without limitation, in the form of a powder, capsule, tablet, softgel, chewable composition, spray, extract, isolate, tea, or decoction that could be derived from one or more portions of the plant such as the root, leaves, stem, aerial portion, whole plant, flowers, or berries, or it could be a chemically synthesized version of an active antiviral chemical found naturally in the plant.

Below are more detailed descriptions of each of the nine components, listed alphabetically, which in various combinations comprise the present invention. It is important that doses be sufficient to provide antiviral effectiveness, and the normal range of total daily dosages for each component is given.

*Andrographis* is also known as *Andrographis paniculata* or King of Bitters. Based on the literature, effective daily antiviral doses of *Andrographis* for adults lie in the ranges of 1-8 g whole plant powder (which can be made into a tea or decoction), 500-2500 mg plant extract, 100-400 mg leaf extract, or 30-120 mg andrographolide (the active antiviral substances).

*Astragalus* is also known by the common names of milk vetch, bei qi, huang qi, ogi, hwanggi and the botanical names of *Astragalus membranaceus* and *Astragalus mongholicus*. Effective daily antiviral doses of *Astragalus* for adults lie in the ranges of 1-8 g powdered root, 200-2000 mg extract, or 3-20 mg astragaloside IV.

*Eleuthero* is also known by the common names of Siberian Ginseng, Siberian *Eleuthero*, Russian ginseng, devil's shrub, touch-me-not, wild pepper, shigoka, and ci wu jia, and its botanical names *Eleutherococcus senticosus* and *Acanthopanax senticosus*. Effective daily antiviral doses of *Eleuthero* for adults lie in the ranges of 2-8 g root powder, 250-1500 mg extract, 0.5-10 mg eleutheroside B, and 1-10 mg eleutheroside E.

*Isatis* is also known by the common names indigo wood, Chinese indigo, woad, glastum, Qing Dai, and Ban Lan Gen, as well as the botanical names *Isatis indigotica, Isatis tinctoria*, and *Radix isatidis* baphicacanthi. Effective daily antiviral doses of *Isatis* for adults lie in the ranges of 5-60 g root powder or 1-10 g of extract granules.

*Lomatium* is also known as *Lomatium Dissectum*, Indian Balsam, Indian carrot, desert parsley, fernleaf biscuitroot, and Indian consumption plant. Effective daily antiviral doses of *Lomatium* for adults lie in the range of 0.5-20 mL of extract or isolate, or 50-1500 mg of extract powder.

*Pelargonium* is also known as *Pelargonium sidoides*, South African geranium, Umckaloabo, kalwerbossie, Rabassamin, and Zucol. Effective daily antiviral dosages of *Pelargonium* for adults lie in the range of 1-15 mL of 1:5 liquid extract and 30-300 mg of root extract powder.

*Sambucus* is also known as *Sambucus nigra*, Elderberry, Black Elderberry, Boor Tree, Bounty, Common Elder, Ellanwood, European Alder, and European Black Elder. Effective daily antiviral dosages of *Sambucus* for adults lie in the range of 100 mg to 20 g extract or 15-75 mL syrup standardized to 30-38% elderberry.

*Scute* is also known as Chinese skullcap, *Scutellaria baicalensis, Scutellariae radix*, Baical skullcap, Ban Zhi Lian, huang qin (Mandarin), and ogon (Japanese). It has been used in traditional Chinese medicine, primarily for its calming effect. Effective daily antiviral dosages of *Scute* for adults lie in the range of 6-15 g powder, 1-15 mL of 4:1 extract, or 500-1000 mg solid extract powder.

Zinc is also known as zinc ions, is often supplied in the form of zinc acetate, zinc citrate, zinc gluconate, zinc glycerinate, zinc picolinate, or zinc sulfate, and is also contained in other zinc compounds. Effective daily antiviral dosages of Zinc for adults lie in the range of 80-200 mg/day.

Combinations of the components listed above may be created by taking individual supplements simultaneously, or more than one can be combined into the same delivery vehicle such as a capsule, tablet, softgel, lozenge, chewable tablet, powder, spray, syrup, extract, or isolate. The important point is that the synergistic composition is formed in the body of the person taking the supplements. The mixture can be created either during manufacturing, by mixing components physically in the delivery vehicle, or alternately may be formed in the body of the consumer as separate components are taken simultaneously, or by a combination of both methods. In other words, some components may be delivered in mixed form and some in separate form (to facilitate convenience of dosage, ease of manufacturing, and low cost), ultimately forming the same mixture in the body, with the same effectiveness regardless of whether pre-mixed or mixed in the body.

The more expensive components of the nine, per dose and course of treatment, are *Isatis, Lomatium*, and *Pelargonium*. Therefore compositions minimizing or leaving out one or more of these components, if effective for the desired purpose, would have a cost advantage. Therefore, one preferred low-cost embodiment, leaving out these three components, is a combination of *Andrographis, Astragalus, Eleuthero, Sambucus, Scute*, and Zinc.

To the blends listed herein, additional components may be added, as well as inactive excipients. Other possible components may include, for example, without limitation: beta-glucan, dimethlyglycine, echinacea, eucalyptus oil, forsythia, garlic, ginger, goldenseal, grape seed, green tea, humic acid, hyssop, Japanese honeysuckle, lemon balm, licorice, lonicera, Maitake mushroom, mullein, N-acetyl-cysteine, olive leaf, propolis, Reishi mushroom, St. John's wort, schizandra, vitamin C, and vitamin E.

The present invention can be illustrated with the following non-limiting examples. Examples 1 and 2 are representative of the dozen real human tests conducted.

Example 1

*Eleuthero, Sambucus*, and Zinc

A 52-year-old man noticed a sore throat that persisted for a few hours and was getting worse, indicating an impending cold or flu. He promptly began taking Zinc lozenges once every two hours for two days (each containing 23 mg as gluconate and citrate), plus three-times-daily doses for four days of *Eleuthero* capsules (each containing 200 mg extract standardized to 0.2% Eleutheroside B and 0.5% Eleutheroside E) and *Sambucus* syrup (1 tsp containing 800 mg extract). The sore throat was gone within 24 hours and no further symptoms developed. As a completely unexpected and surprising additional benefit, the Herpes Type 2 outbreaks that he had been experiencing every few months ceased immediately and have not recurred for over seven years.

Example 2

*Andrographis, Astragalus, Eleuthero, Sambucus*, and Zinc

A 49-year-old woman in good health noticed a sore throat developing in the evening and promptly started the following regimen using bottles of supplements that had been obtained beforehand: three times a day for four days the following set of supplements: *Eleuthero* (capsule containing 200 mg extract standardized to 0.2% Eleutheroside B and 0.5% Eleutheroside E), a chewable *Sambucus* tablet (containing 100 mg extract), plus *Andrographis* (tablet, 400 mg) and *Astragalus* (capsule, 500 mg standardized extract). Zinc lozenges (each containing 23 mg as gluconate and citrate, plus 60 mg Vitamin C and 20 mg Echinacea) were taken every two hours for two days. On the next day a mild sore throat remained, but it was gone the following morning and no further symptoms developed.

The following paragraphs describe hypothetical examples illustrating the expected outcomes of future scenarios, using the present invention.

Example 3

Convenient Liquid Extract Form

One embodiment of the present invention consists of a convenient liquid form. Using this embodiment, at the first signs of cold or flu the patient can open the Liquid Herbal Remedy Kit, which contains a bottle of all-natural herbal extract blend plus a package of zinc lozenges. The bottle of all-natural herbal extract blend contains mixed extracts of *Andrographis, Astragalus, Eleuthero, Isatis, Lomatium, Pelargonium, Sambucus*, and *Scute*, in the proper concentrations to provide effective antiviral doses when the mixture is taken at the recommended dosage. Three times a day the patient simply mixes the specified volume (e.g., 15 mL=1 tbsp) of the liquid extract blend into juice or water and drinks it. The patient also takes the zinc lozenges every two to three hours (a total of four to six per day). The symptoms remain very mild and are gone on the third day. The all-natural herbal extract blend has the additional advantages that it is more convenient than taking capsules or tablets, and also applies the herbal extracts topically to the throat while being swallowed. The all-natural herbal extract blend could of course also be sold separately from zinc lozenges. A form of the liquid extracts with Zinc included in the liquid could also be produced by the addition of Zinc (as zinc citrate, picolinate, sulfate, or another bioavailable ionic form), eliminating the need for separate Zinc lozenges, and also making the combination of supplements easier to take for both adults and children.

Example 4

Severe Flu Pandemic

In the future it is likely that at some time a new, highly transmissible, high-mortality strain of flu virus will be spreading rapidly around the globe. When that happens, it is quite possible that a vaccine against it will not be available for months, and medical care facilities could be overwhelmed. Families can take precautions, including avoiding public places as much as possible and sanitizing hands frequently. If, despite these efforts, one family member starts to develop symptoms, it exposes all family members to risk of infection. It would be fortunate if they have kits of antiviral supplements on hand for each family member, including kits usable by children that provide smaller dosages. They can open a kit for the affected family member and start the following course of treatment for five days: Three times a day (with food) the family member takes tablet/capsule supplements, containing *Andrographis, Astragalus, Eleuthero, Isatis*, and *Scute*, followed by lozenge supplements containing *Lomatium, Pelargonium, Sambucus*, and Zinc. Or, alternatively, the affected family member could take the All-Natural Herbal Extract Blend as described above plus Zinc lozenges. With either course of treatment the symptoms are expected to remain very mild, and to be entirely gone after a short time, thereby protecting not only the individual affected but also other family members and the general public.

Example 5

*Sambucus* and *Scute*

It is anticipated that *Scute* will demonstrate similar synergistic effects with *Sambucus* to those demonstrated by *Eleuthero* and Zinc. Therefore it is expected that a patient faced with a possible developing cold or flu can take three daily doses of *Sambucus* and *Scute* to achieve similar results to taking *Sambucus* with *Eleuthero* and Zinc, in other words rapid diminution and elimination of symptoms. Additional components may further enhance the effectiveness.

Example 6

Cell Culture

In the laboratory, a human cell culture is infected with Influenza A virus. A mixture of *Eleuthero Sambucus*, and Zinc is administered. It is expected that the combination will be found to be much more effective at inhibiting viral reproduction than any single component or their additive effect, validating the synergistic effect. Similarly, it is expected that a combination of *Sambucus* and *Scute* will also show synergistic viral inhibition.

Example 7

Norovirus

It is expected that the present invention will help relieve norovirus infections. If someone works at an office where there is an outbreak of the highly contagious norovirus, and starts to feel nausea and stomach cramps, two of the early symptoms, the person can start promptly on the following regimen: three times a day (mixed in water or juice) a dose is taken of combined liquid extract supplements containing *Andrographis, Astragalus, Eleuthero, Isatis, Lomatium, Pelargonium, Sambucus*, and *Scute*. Five times a day Zinc lozenge supplements are taken. It is expected that the symptoms will remain mild for two days, and be gone on the third day.

Example 8

Hepatitis

It is expected that the present invention will benefit hepatitis patients. For example, a person diagnosed with Hepatitis B could apply the following regimen for six weeks: three doses per day of *Andrographis, Astragalus, Isatis, Pelargonium*, and *Scute*, supplemented as needed with conventional drugs and therapy. It is expected that at the end of six weeks the viral load and symptoms will be significantly reduced, and liver function improved.

Example 9

HIV

It is also expected that the present invention will help those infected with human immunodeficiency virus (HIV). For example, someone suffering from HIV infection, along with conventional treatment, can take orally a combination of *Sambucus, Scute, Lomatium, Pelargonium*, Beta Glucans, and Olive Leaf extract in two daily doses for six weeks. At the end of this time the viral load is expected to be decreased significantly more than with conventional treatment alone.

Example 10

Canine Influenza

It is expected that pets and livestock will benefit from the present invention. For example, if a pet owner notices that a dog is sneezing, coughing, and has fever and nasal discharge, the veterinarian's diagnosis may be canine influenza. The owner could provide the following supplements, in dosages based on body weight, mixed with food in a form palatable to the dog, twice a day: *Andrographis, Eleuthero, Isatis, Lomatium, Pelargonium, Sambucus*, and *Scute*.

Example 11

Bovine Respiratory Syncytial Virus

If a cow is noticed to have a fever, rapid breathing, and nasal discharge, the diagnosis could be bovine respiratory syncytial virus. In dosages commensurate with its body size, a relatively low-cost supplement mixture can be mixed into its daily feed, consisting of *Andrographis, Eleuthero, Sambucus*, and *Scute*. After a few days the symptoms subside and the cow is healthy. Administering the present invention to an animal may well help rid it of other viral diseases that may be present.

The present invention provides a number of advantages, several of which are described below.

One of the major dangers of colds and flu is secondary bacterial infection such as bronchitis, pneumonia, sinusitis, or otitis. By reducing viral damage to membranes and other tissues that makes them more susceptible to bacterial attack, and by boosting immunity, the present invention reduces the danger of secondary bacterial infection.

In many cases the supplements are only taken for a few days when needed, thus reducing the cost compared to taking preventative supplements on a long-term basis, and reducing risks of side-effects resulting from long-term exposure.

The supplements provide some additional health benefits other than antiviral activity. For example, some have antibacterial, antifungal, anti-inflammatory, cardioprotective, or calming properties.

To summarize, the advantages of the present invention include, without limitation: (1) the action of the components is synergistic in combatting viral infections, (2) the invention is effective against a broad range of viruses, (3) other concurrent viral infections in the patient may also be resolved, (4) because damage to bodily tissues is greatly reduced, and immunity is boosted, the likelihood of secondary infections is greatly reduced, (5) because of the nature of the components and the brief period during which they are taken, side effects are minimal or nonexistent for most people, (6) a prescription is not required, (7) the active ingredients are all natural (8) there are public health benefits reduced contagion and transmission of disease, (9) there are substantial economic benefits to both individuals and society as a whole because of the reduction in lost work days and doctor visits, (10) it is difficult for viruses to develop resistance, (11) cost is low compared to other treatment options, (12) in contrast to some other blends, the components are provided in effective quantities and these quantities are revealed to consumers in the labeling, (13) component selection is based on scientific evidence of antiviral effectiveness, (14) components are combined in such a way as to provide multiple mechanisms of action against viral agents, (15) additional health benefits are gained by the consumer in addition to antiviral action, (16) components can be packaged in a convenient form for correct dosage and timing, and (17) in one embodiment, a kit for a single course of treatment prevents potential transfer of viral contamination to other users through handling.

The present invention also encompasses methods of use that consist of providing for oral consumption effective, regular antiviral doses of certain combinations of supplements selected from the group consisting of: *Andrographis, Astragalus, Eleuthero, Isatis, Lomatium, Pelargonium, Sambucus, Scute*, and Zinc.

Descriptions of Embodiments

Different embodiments of the invention may involve different numbers of these nine components, may vary in the forms in which the supplements are provided, may vary in dosages, and may contain additional ingredients.

In one embodiment of the present invention, *Eleuthero, Sambucus* and Zinc are provided in a composition comprising at least 3% of *Eleuthero*, and at least 3% *Sambucus*, by weight of the herbal portion of the composition. These can be provided in the form of capsules, tablets, chewable tablets, liquid extract, or a mixture of these methods.

In other embodiments, to the composition comprising *Eleuthero, Sambucus*, and Zinc are added one or more additional components selected from the group comprising: *Andrographis, Astragalus, Isatis, Lomatium, Pelargonium*, and *Scute*.

In one embodiment of the invention, a combination of *Sambucus* and *Scute* is provided as capsules, tablets, chewable tablets, liquid extracts, or a mixture of these methods.

In other embodiments, to the composition comprising *Sambucus* and *Scute* are added one or more additional components selected from the group comprising: *Andrographis, Astragalus, Eleuthero, Isatis, Lomatium, Pelargonium*, and Zinc.

In one embodiment of the present invention, a bottle holding liquid all-natural herbal extract blend is provided, containing mixed extracts and/or isolates of *Andrographis, Astragalus, Eleuthero, Isatis, Lomatium, Pelargonium, Sambucus*, and *Scute*. To combat a developing cold or flu, the liquid is added in the correct dosage (e.g., 1 tablespoon=15 mL for adults) to juice or water three times a day and taken with meals.

In one embodiment of the present invention, a kit designed to provide one course of treatment is provided. In this kit, at least two compositions are packaged separately in a single overall package.

In one embodiment of the present invention the kit contains zinc lozenges plus a bottle holding approximately six fluid ounces of the all-natural herbal extract blend.

In one embodiment of the present invention, the kit contains dosage packs and instructions. Each dosage pack contains two to seven single-dose sets of lozenges and/or chewable tablets, plus one to five single-dose sets of capsules and/or tablets.

In one embodiment of the present invention the kit contains both dosage packs as described above, plus a dropper bottle. The dropper bottle contains a mixture of those components deemed most effective and economical to provide as isolates or extracts.

In one embodiment of the present invention, sterilized antiviral components are provided by intravenous injection.

One embodiment of the invention, for example, without limitation, is a kit designed for a single course of treatment for one person. The kit is contained in an outer package that has proper labeling, including instructions and warnings. Within the outer package is a bottle containing mixed isolates and extracts of *Andrographis, Astragalus, Eleuthero, Isatis, Lomatium, Pelargonium, Sambucus*, and *Scute*, with instructions to take three daily doses of liquid mixed in drinks. The kit also contains a packet of Zinc lozenges, with instructions to take four to six lozenges a day.

In another embodiment, the bottle of liquid mixed isolates and extracts can be provided as a stand-alone product (not in a kit).

In another embodiment, within a kit are contained three to six "daily dosage packs." Each "daily dosage pack" contains two to four "tablet/capsule packs" plus three to six "lozenge packs." Each "tablet/capsule pack" contains tablets and/or capsules containing doses of *Andrographis, Astragalus, Eleuthero, Isatis, Pelargonium*, and *Scute*. Each "lozenge pack" contains lozenges with effective antiviral doses of Zinc, *Sambucus, Pelargonium*, and *Lomatium*.

In another embodiment a dropper bottle is included with the kit, when it is deemed preferable to provide extracts or isolates of one or more component(s) in liquid form. For example, in one embodiment *Lomatium* comes in liquid form, and the lozenges and chewable tablets contain separate components. This embodiment of the kit for a course of treatment includes four daily dosage packs. Each daily dosage pack contains three individual dosage packs of capsules, each pack containing *Andrographis, Astragalus, Eleuthero, Isatis*, and *Scute*. Instructions direct the consumer to take a pack of capsules and tablets morning and evening, with food. The daily dosage pack also includes four packets, each packet containing three chewable tablets: Zinc, *Sambucus*, and *Pelargonium*. Instructions direct the consumer to take a packet of chewable tablets four times a day. A dropper bottle of *Lomatium* isolate included with the kit instructs the user to take three droppersful of the isolate in a drink three times a day.

In another embodiment, the kit contains four daily dosage packs, one for each day of treatment. Each daily dosage pack contains three individual dosage packs of capsules and tablets, and each of these individual dosage packs contains *Andrographis, Astragalus, Eleuthero, Isatis*, and *Scute* (all of which are commercially available in powdered extract form). Instructions direct the consumer to take the pack of capsules at mealtimes, with food. Each daily dosage pack also includes four chewable tablets, each chewable tablet containing a mixture of Zinc, *Sambucus, Pelargonium*, and *Lomatium*. Instructions direct the consumer to take a chewable tablet four to six times a day.

In another embodiment, a kit is designed for use by a child. In this embodiment, the dosages in the capsules and tablets are half those of the previous embodiments which are designed for adults. It would also be possible for a child to take half the adult dose of the all-natural herbal extract blend described above by simply measuring out half the volume of liquid (e.g., ½ tbsp=7.5 ml). Of course larger kits could also be made for multiple consumers and multiple courses of treatment.

In yet another embodiment a method is provided for administering a dose of antiviral supplement for the purpose of inhibiting viral infections, comprising the step of administering, to a human or animal, a dietary supplement comprising an ingredient obtainable from *Eleuthero*, an ingredient obtainable from *Sambucus*, and Zinc, in which the ingredient obtainable from *Eleuthero* composes at least 3%, and an ingredient obtainable from *Sambucus* comprises at least 3%, of the weight of the total herbal portion of the dietary supplement.

In a further embodiment a method is provided for inhibiting viral infections, comprising the step of administering, to a human or animal, a dietary supplement comprising an ingredient obtainable from *Sambucus* and an ingredient obtainable from *Scute*.

In yet a further embodiment a method is described of providing a kit containing a course of supplements.

I claim:
1. An antiviral composition comprising:
   0.2% to 40% Zinc;
   at least 3% by dry weight of a water or ethanol or ethanol/water extract of *Eleuthero*;
   and at least 3% by dry weight of a water or ethanol or ethanol/water extract of *Sambucus*.
2. The composition of claim 1 comprising 10% to 65% of the extract from *Eleuthero*, 25% to 85% of the extract from *Sambucus*, and 0.2% to 10% Zinc.
3. The composition of claim 1 wherein the quantity of *Eleuthero* per daily dose contains between 200 mg and 1500 mg root extract.
4. The composition of claim 1 wherein the quantity of *Eleuthero* per daily dose contains between 0.5 mg and 10 mg eleutheroside B.
5. The composition of claim 1 wherein the quantity of *Eleuthero* per daily dose contains between 1 mg and 10 mg eleutheroside E.
6. The composition of claim 1 wherein the quantity of *Sambucus* per daily dose contains between 100 mg and 20 g extract.
7. The composition of claim 1 wherein the quantity of Zinc per daily dose is between 60 mg and 250 mg.
8. The composition of claim 1 further comprising a water or ethanol or ethanol/water extract of *Andrographis*.
9. The composition of claim 1 further comprising a water or ethanol or ethanol/water extract of *Astragalus*.
10. The composition of claim 1 further comprising a water or ethanol or ethanol/water extract of *Isatis*.
11. The composition of claim 1 further comprising a water or ethanol or ethanol/water extract of *Lomatium*.
12. The composition of claim 1 further comprising a water or ethanol or ethanol/water extract of *Pelargonium*.
13. The composition of claim 1 further comprising a water or ethanol or ethanol/water extract of *Scute*.
14. The composition of claim 1 further comprising one or more additional component(s) selected from the group consisting of: beta-glucan, dimethlyglycine, *echinacea, eucalyptus*, forsythia, garlic, ginger, goldenseal, grape seed, green tea, humic acid, hyssop, Japanese honeysuckle, lemon balm, licorice, lonicera, Maitake mushroom, mullein, N-acetyl-cysteine, olive leaf, propolis, Reishi mushroom, St. John's wort, schizandra, vitamin C, and vitamin E.
15. The composition of claim 1 comprising one or more additional component(s) selected from the group consisting of: alcohol, artificial colors, artificial flavors, citric acid, corn starch, dextrin, dibasic calcium phosphate, fructose, gelatin, hydroxypropylmethylcellulose, magnesium stearate, malic acid, maltodextrin, mannitol, microcrystalline cellulose, modified cellulose gum, natural colors, natural flavors, silica, sorbitol, stearic acid, sucrose, and xylitol.
16. The composition of claim 1 wherein at least two compositions are packaged separately in a single overall package (a kit).
17. The composition of claim 16 wherein the kit contains dosage packs.
18. The composition of claim 16 wherein the kit comprises components selected from the group comprising: tablets, capsules, lozenges, hard candies, oral sprays, nasal sprays, elixirs, and sterilized solutions for injection.
19. A method for inhibiting viral infections comprising the step of administering, to a human or animal, a dietary supplement comprising the composition of claim 1.
20. The method of claim 19, wherein the step of administering the composition is carried out one to six times a day.

21. The method of claim 19, wherein the composition is administered in a form selected from the group comprising: tablets, capsules, lozenges, chewable compositions, troches, hard candies, oral sprays, nasal sprays, gels, powders, extracts, isolates, elixirs, syrups, teas, decoctions, liquid solutions, liquid suspensions, and sterilized solutions for injection.

22. The method of claim 19 wherein wherein at least two compositions are packaged separately in a single overall package (a kit).

23. The method of claim 22 wherein the kit contains dosage packs.

24. The composition of claim 1 further comprising at least one water or ethanol or ethanol/water extract selected from the group comprising: *Andrographis, Astragalus, Forsythia, Isatis, Lomatium, Lonicera, Pelargonium*, and *Scute*.

\* \* \* \* \*